US009302200B2

(12) United States Patent
Timken et al.

(10) Patent No.: US 9,302,200 B2
(45) Date of Patent: Apr. 5, 2016

(54) ALKYLATION PROCESS UNIT WITH RECYLE OF HYDROGEN AND RECOVERY OF HYDROGEN CHLORIDE

(71) Applicants: Hye Kyung Cho Timken, Albany, CA (US); Bong-Kyu Chang, Novato, CA (US)

(72) Inventors: Hye Kyung Cho Timken, Albany, CA (US); Bong-Kyu Chang, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 565 days.

(21) Appl. No.: 13/901,935

(22) Filed: May 24, 2013

(65) Prior Publication Data

US 2014/0037512 A1    Feb. 6, 2014

Related U.S. Application Data

(60) Division of application No. 13/563,355, filed on Jul. 31, 2012, and a continuation of application No. 13/563,385, filed on Jul. 31, 2012, now Pat. No. 9,233,316, and a continuation of application No. 13/563,415, filed on Jul. 31, 2012, now Pat. No. 8,704,018.

(51) Int. Cl.
*B01J 8/00* (2006.01)
*C07C 2/54* (2006.01)
*B01J 38/10* (2006.01)
(Continued)

(52) U.S. Cl.
CPC ............... *B01D 3/009* (2013.01); *B01J 38/10* (2013.01); *C07C 2/54* (2013.01); *C07C 2/58* (2013.01); *C07C 2527/125* (2013.01); *Y02P 20/582* (2015.11); *Y02P 20/584* (2015.11)

(58) Field of Classification Search
None
See application file for complete search history.

(56) References Cited

U.S. PATENT DOCUMENTS

| 3,476,825 | A | * | 11/1969 | Hutson, Jr. et al. | ....... C07C 2/60 502/53 |
| 5,310,713 | A | * | 5/1994 | Kojima | ................... B01J 23/96 502/30 |
| 5,421,167 | A | | 6/1995 | Verma | |

(Continued)

OTHER PUBLICATIONS

Sinnott, Chemical Engineering Design, Coulson & Richardson's Chemical Engineering, vol. 6 Fourth Edition, 5 pages, 2005.

*Primary Examiner* — Jennifer A Leung
(74) *Attorney, Agent, or Firm* — Susan M. Abernathy

(57) ABSTRACT

We provide alkylation process units, one comprising:
  a) a hydrogenation reactor that produces a regenerated catalyst effluent;
  b) a fractionation unit that separates the effluent into gas and light hydrocarbon;
  c) a connection between the fractionation unit for transmitting the gas to the hydrogenation reactor; and
  d) a connection between the fractionation unit and an alkylation reactor to transmit the light hydrocarbon to the alkylation reactor. The other comprising:
  a) a separator, connected between the hydrogenation reactor and a fractionation unit; that separates the effluent into gas and liquid; and wherein the fractionation unit separates a hydrocarbon stream from the liquid into a light hydrocarbon comprising a hydrogen chloride and an extracted conjunct polymer naphtha;
  b) a connection between the separator and the hydrogenation reactor for transmitting the gas to the hydrogenation reactor; and
  c) a connection between the fractionation unit and an alkylation reactor to transmit the light hydrocarbon.

8 Claims, 6 Drawing Sheets

An Alkylation Unit with Catalyst Hydro-Regeneration, Hydrogen Recycle, and Hydrogen Chloride Recovery

(51) Int. Cl.
  *B01D 3/00*   (2006.01)
  *C07C 2/58*   (2006.01)

(56) References Cited

U.S. PATENT DOCUMENTS

| | | | |
|---|---|---|---|
| 6,395,945 B1 | 5/2002 | Randolph | |
| 7,432,408 B2 | 10/2008 | Timken et al. | |
| 7,432,409 B2 | 10/2008 | Elomari et al. | |
| 7,553,999 B2 | 6/2009 | Elomari et al. | |
| 7,569,740 B2 | 8/2009 | Elomari | |
| 7,576,252 B2 | 8/2009 | Elomari et al. | |
| 7,651,970 B2 | 1/2010 | Elomari et al. | |
| 7,678,727 B2 | 3/2010 | Harris et al. | |
| 7,691,771 B2 | 4/2010 | Harris et al. | |
| 7,732,363 B2 | 6/2010 | Elomari et al. | |
| 7,732,364 B2* | 6/2010 | Chang | B01J 31/40 502/150 |
| 7,732,651 B2 | 6/2010 | Driver et al. | |
| 7,825,055 B2 | 11/2010 | Elomari et al. | |
| 7,919,664 B2 | 4/2011 | Hommeltoft et al. | |
| 7,923,593 B2 | 4/2011 | Hommeltoft et al. | |
| 7,923,594 B2 | 4/2011 | Hommeltoft | |
| 7,955,495 B2 | 6/2011 | Hommeltoft et al. | |
| 8,101,809 B2 | 1/2012 | Elomari et al. | |
| 8,124,821 B2 | 2/2012 | Elomari et al. | |
| 2004/0133056 A1* | 7/2004 | Liu | C07C 2/58 585/721 |
| 2007/0142215 A1* | 6/2007 | Harris | B01J 27/125 502/53 |
| 2009/0170687 A1* | 7/2009 | Luo | B01J 8/0453 502/22 |
| 2009/0242840 A1 | 10/2009 | Olschimke et al. | |
| 2010/0147740 A1 | 6/2010 | Elomari et al. | |
| 2011/0155632 A1* | 6/2011 | Timken | C10G 7/00 208/16 |
| 2011/0226669 A1* | 9/2011 | Timken | B01J 31/0277 208/134 |
| 2012/0024750 A1* | 2/2012 | Zhan | C10G 29/205 208/56 |
| 2012/0283500 A1* | 11/2012 | Liu | B01J 31/0278 585/707 |
| 2013/0066130 A1 | 3/2013 | Luo et al. | |
| 2013/0066132 A1 | 3/2013 | Cleverdon et al. | |
| 2013/0066133 A1 | 3/2013 | Cleverdon et al. | |

* cited by examiner

An Alkylation Unit with Catalyst Hydro-Regeneration, Hydrogen Recycle, and Hydrogen Chloride Recovery

H₂ Recycle and HCl Recovery from Ionic Liquid Catalyst Hydrogenation, Comparison Case H₂ Recycle and HCl Recovery from Ionic Liquid Catalyst Hydrogenation H₂ Recycle and HCl Recovery from Ionic Liquid Catalyst Hydrogenation H₂ Recycle and HCl Recovery from Ionic Liquid Catalyst Hydrogenation Hydro-regeneration Process Without Hydrocarbon Extraction Solvent

ALKYLATION PROCESS UNIT WITH RECYLE OF HYDROGEN AND RECOVERY OF HYDROGEN CHLORIDE This application is a divisional of U.S. patent application Ser. No. 13/563,355, filed Jul. 31, 2012, in Group Art Unit 1772; and herein incorporated in its entirety. This application is also a continuation of U.S. patent application Ser. Nos. 13/563,385 and 13/563,415, both filed Jul. 31, 2012, and herein incorporated in their entireties.

TECHNICAL FIELD

This application is directed to processes and process units for improved hydrogen chloride recovery in an ionic liquid alkylation plant using hydro-regeneration of the ionic liquid catalyst.

BACKGROUND

Improved alkylation processes and equipment are needed to provide more efficient operation, including recycling of hydrogen to a hydrogenation reactor, and recovery and recycling of hydrogen chloride to an alkylation reactor.

SUMMARY

This application provides an alkylation process unit, comprising:
  a) a hydrogenation reactor, wherein a used catalyst comprising an ionic liquid catalyst and a chloride produces a regenerated catalyst effluent;
  b) a fractionation unit fluidly connected to the hydrogenation reactor, that separates at least a portion of the regenerated catalyst effluent into a gas fraction comprising a hydrogen gas and into a light hydrocarbon fraction comprising a hydrogen chloride;
  c) a first connection between the fractionation unit and the hydrogenation reactor for transmitting at least a part of the gas fraction to the hydrogenation reactor; and
  d) a second connection between the fractionation unit and an alkylation reactor to transmit at least an amount of the light hydrocarbon fraction to the alkylation reactor.

This application also provides an alkylation process unit, comprising:
  a) a hydrogenation reactor, wherein a used catalyst comprising an ionic liquid catalyst and a chloride produces a regenerated catalyst effluent;
  b) a separator, fluidly connected between the hydrogenation reactor and a fractionation unit; wherein the separator separates the regenerated catalyst effluent into a gas fraction comprising a hydrogen gas and into a separated liquid; and wherein the fractionation unit separates a hydrocarbon stream from the separated liquid into a light hydrocarbon fraction comprising a hydrogen chloride and an extracted conjunct polymer naphtha;
  c) a first connection between the separator and the hydrogenation reactor for transmitting at least a part of the gas fraction to the hydrogenation reactor; and
  d) a second connection between the fractionation unit and an alkylation reactor to transmit at least an amount of the light hydrocarbon fraction to the alkylation reactor.

DETAILED DESCRIPTION

Figure 1:
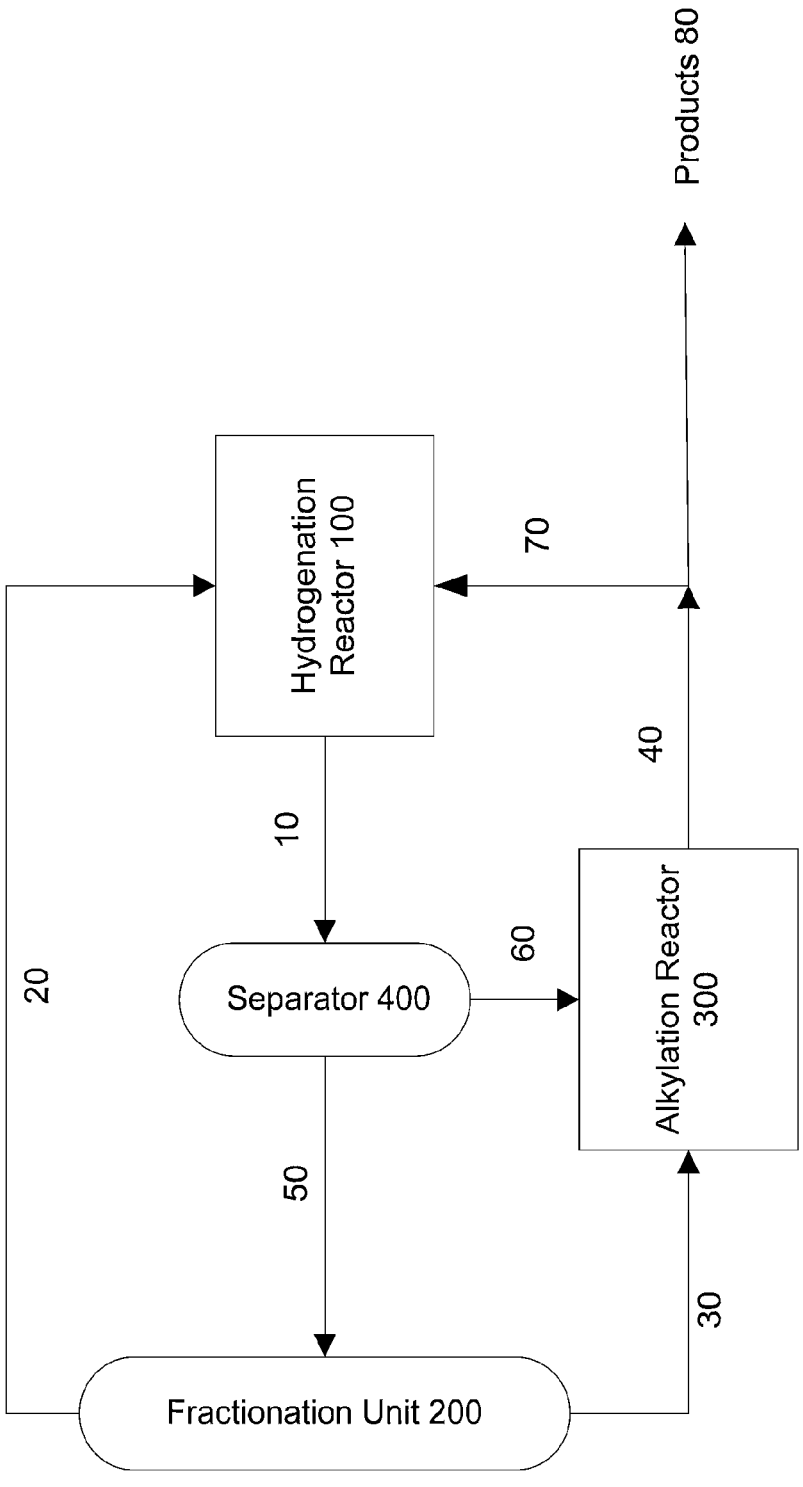
FIG. 1 is a diagram of an alkylation process unit with catalyst hydro-regeneration, hydrogen recycle and hydrogen chloride recovery; the comprehensive case.

Alkylation processes and alkylation process units are used to make alkylate products, including alkylated aromatics and alkylated isoparaffins. The alkylate products can have a broad range of uses including, for example, gasoline blending components, middle distillates, base oils, and petrochemical components. The catalysts used in these processes for alkylation comprise ionic liquid catalyst and a chloride. These catalysts become deactivated during use and require regeneration. The deactivation is at least in part caused by the build-up of conjunct polymer in the ionic liquid catalyst. Regeneration is achieved in a hydrogenation reactor (also referred to herein as a hydro-regeneration reactor). The regenerating removes the conjunct polymer from the ionic liquid catalyst, thus increasing the acidity and ability of the ionic liquid catalyst to perform alkylations.

Since the hydrogenation process uses excess amounts of hydrogen gas, it is highly desirable to be able to recycle the hydrogen gas to the hydrogenation reactor in order to minimize the hydrogen consumption. To maintain good performance of the hydrogenation reactor, the recycled hydrogen gas needs to have high purity, with only a small amount of light hydrocarbons, hydrogen chloride, and other impurities.

In one embodiment, because the used catalyst includes a chloride-containing conjunct polymer, the hydrogenation unit liberates hydrogen chloride, which can build up to excessive levels upon recycling and can suppress conversion in the hydrogenation reactor unless it is removed. Conventional acid gas treating methods, for example, caustic aqueous scrubbing systems, can be used to remove the hydrogen chloride, but then the hydrogen chloride cannot be simply reused in the alkylation process. A comparative example of how an acid gas treating method could be employed in an alkylation plant shown in FIG. 2. When the hydrogen gas containing hydrogen chloride (offgas (50)) is treated with caustic solution, then the hydrogen chloride is converted to a salt that cannot be reused in the alkylation process. For example, if NaOH is used as the caustic reactant, then the HCl is converted to NaCl and water, and the NaCl is not suitable for recycling into an ionic liquid alkylation process. The HCl destroyed in the HCl removal step represents a significant operating cost since it must be compensated for by additional chloride injection into the alkylation unit. It also results in an aqueous waste stream that must be neutralized and disposed of in the water treatment system of the facility. Further, the recycle hydrogen must then be thoroughly dried before use in the hydrogenation reactor. In addition, a significant amount of a recycle gas purge (15) out of the gas fraction comprising the hydrogen gas (20) is needed in order to suppress build up of light hydrocarbons in the recycled gas.

We provide at least four different process configurations in FIGS. 1, 3, 4, and 5, where we can produce a high purity hydrogen gas stream to recycle to the hydrogenation reactor and we can recover and recycle hydrogen chloride to the alkylation reactor. The separation and recycle of hydrogen and the separation, recovery, and recycle of the hydrogen chloride are well integrated with the entire alkylation process to make the process more efficient and economical.

Referring to FIG. 1, it is shown that a hydrogenation reactor (100) can be used continuously with highly efficient hydrogen and hydrogen chloride use in an alkylation process employing an ionic liquid catalyst and a chloride by the following process:

A used catalyst (70) comprising an ionic liquid catalyst and a chloride is regenerated in a hydrogenation reactor (100). The used catalyst (70) is taken from an effluent (40) from the alkylation reactor (300), which is then separated into the used catalyst (70) and the alkylate products (80). The hydrogenation reactor produces a regenerated catalyst effluent (10) which is separated in a separator (400) into an offgas (50) and an ionic liquid catalyst stream (60). The ionic liquid catalyst stream (60) is recycled to the alkylation reactor (300). The offgas (50), which is a portion of the regenerated catalyst effluent (10), is separated in a fractionation unit (200) into a gas fraction comprising a hydrogen gas (20) and a light hydrocarbon fraction comprising a hydrogen chloride (30). At least a part of the gas fraction comprising hydrogen gas (20) is recycled to the hydrogenation reactor (100) and at least an amount of the light hydrocarbon fraction comprising hydrogen chloride (30) is recovered and recycled to the alkylation reactor (300).

The term 'offgas' is defined herein as a gaseous effluent from the hydrogenation reactor. 'Recycling' is defined herein as returning material to a previous stage in a cyclic process. 'Recovering' is defined herein as retaining either in a substantial amount or in full, as opposed to disposing or removing. A substantial amount is at least 50 wt %.

Figure 2:
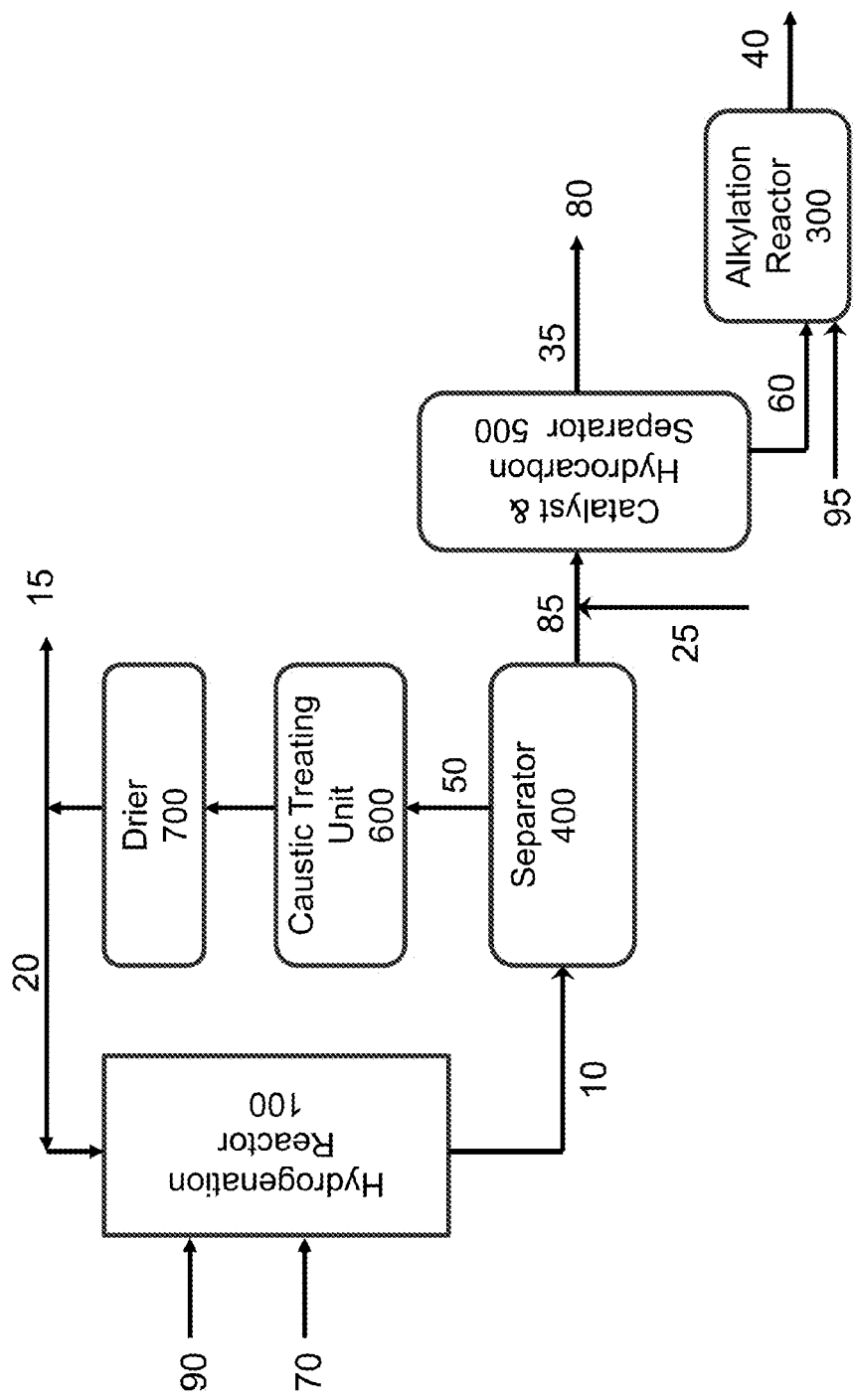
FIG. 2 is a diagram of an alkylation process unit with catalyst hydro-regeneration, hydrogen recycle, and hydrogen chloride removal by caustic scrubbing; the comparison case.

FIG. 2 shows a comparison process unit that does not recover a light fraction comprising a hydrogen chloride. In FIG. 2, hydrogen (90), and used catalyst (70) from an alkylation reactor (300) are regenerated in a hydrogenation reactor. The regenerated catalyst effluent (10) is separated in a separator (400) that is a gas/liquid separation unit. The offgas (50) from the separator is subsequently treated in a caustic treating unit (600) and a drier (700), which remove the hydrogen chloride (as opposed to recovering) to produce a dry gas fraction comprising a hydrogen gas (20). The gas fraction comprising the hydrogen gas (20) is sent to the hydrogenation reactor. A recycle gas purge (15) stream removes excess hydrogen and light hydrocarbons from the process unit. The separated liquid (85) from the separator is mixed with a hydrocarbon extraction solvent (25) and the mixture is fed to an ionic liquid catalyst and hydrocarbon separator (500) which separates the mixture into a stream comprising mixed conjunct polymer and extraction solvent (35) and an ionic liquid catalyst stream (60). The stream comprising mixed conjunct polymer and extraction solvent (35) is sent to the refinery hydrocarbon pool of alkylate products (80). The ionic liquid catalyst stream (60) is recycled to the alkylation reactor (300). Chloride addition (95) is needed to replace the hydrogen chloride that is removed in the caustic treating unit (600).

Figure 3:
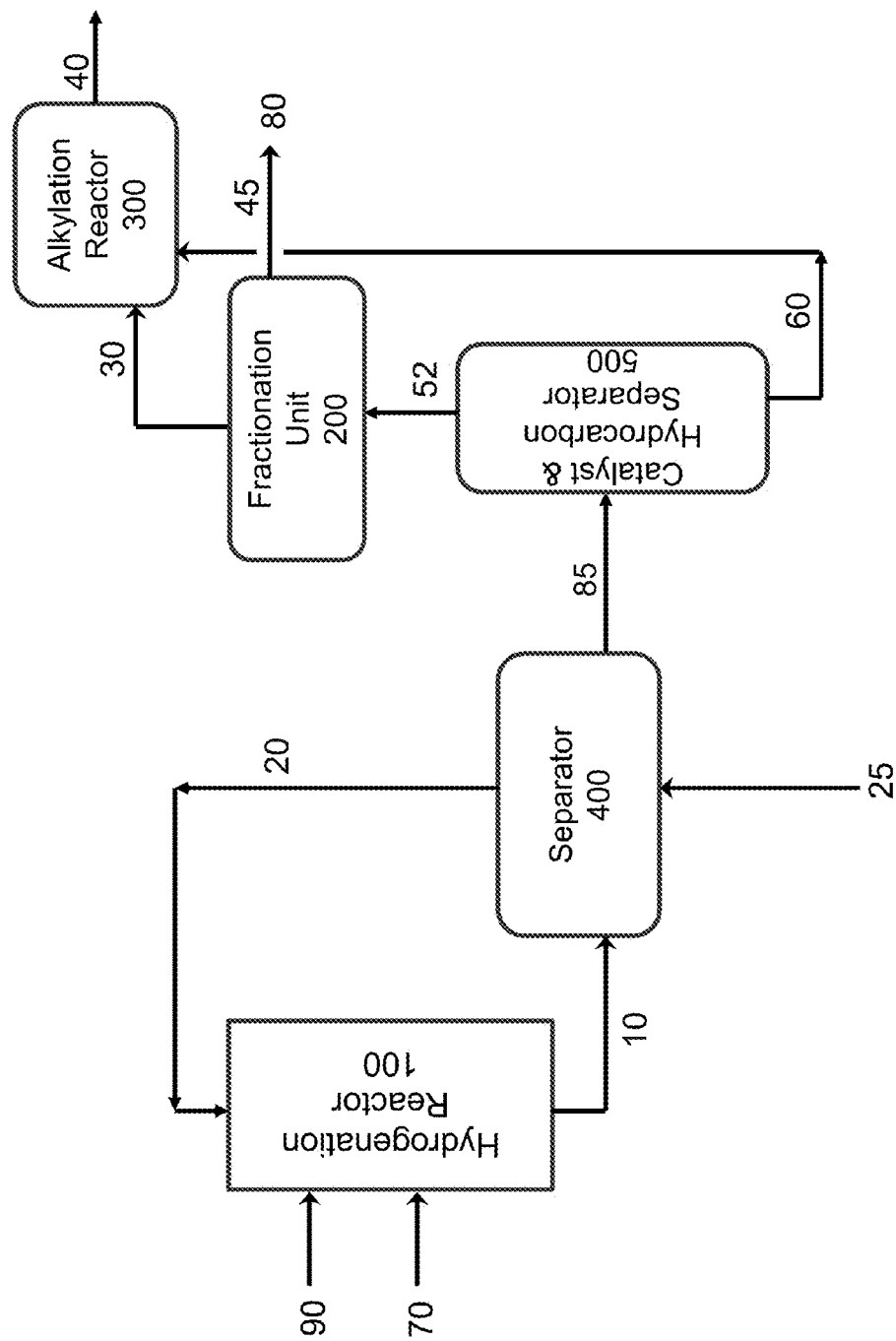
FIG. 3 is a diagram of an alternative alkylation process unit with catalyst hydro-regeneration, hydrogen recycle from a separator, and hydrogen chloride recovery.

FIG. 3 shows an improved process compared to FIG. 2, wherein hydrogen is recycled and hydrogen chloride is recovered and recycled efficiently. In FIG. 3, hydrogen (90), and used catalyst (70) from an alkylation reactor (300) are regenerated in a hydrogenation reactor. The regenerated catalyst effluent (10) is separated in a separator (400) that is a gas/liquid separation unit. A hydrocarbon extraction solvent (25) is fed to the separator (400) such that the separator (400) produces a separated liquid (85) and a gas fraction comprising a hydrogen gas (20). The gas fraction comprising the hydrogen gas (20) has a reduced amount of hydrogen chloride and the gas fraction comprising the hydrogen gas (20) is recycled to the hydrogenation reactor (100). The separated liquid (85) from the separator (400) comprises a hydrogen chloride. The separated liquid (85) is fed to an ionic liquid catalyst and hydrocarbon separator (500), which separates the separated liquid (85) into a hydrocarbon stream (52) and an ionic liquid catalyst stream (60). The hydrocarbon stream (52) is fed to a fractionation unit (200), where it is separated into two streams. One stream is a light hydrocarbon fraction comprising the hydrogen chloride (30). The second stream is extracted conjunct polymer naphtha (45). The light hydrocarbon fraction comprising the hydrogen chloride (30) is also recycled to the alkylation reactor (300). In this process the hydrogen chloride is recovered and recycled, rather than removed, as in FIG. 2. The extracted conjunct polymer naphtha (45) is sent to the refinery hydrocarbon pool of alkylate products (80).

Figure 4:
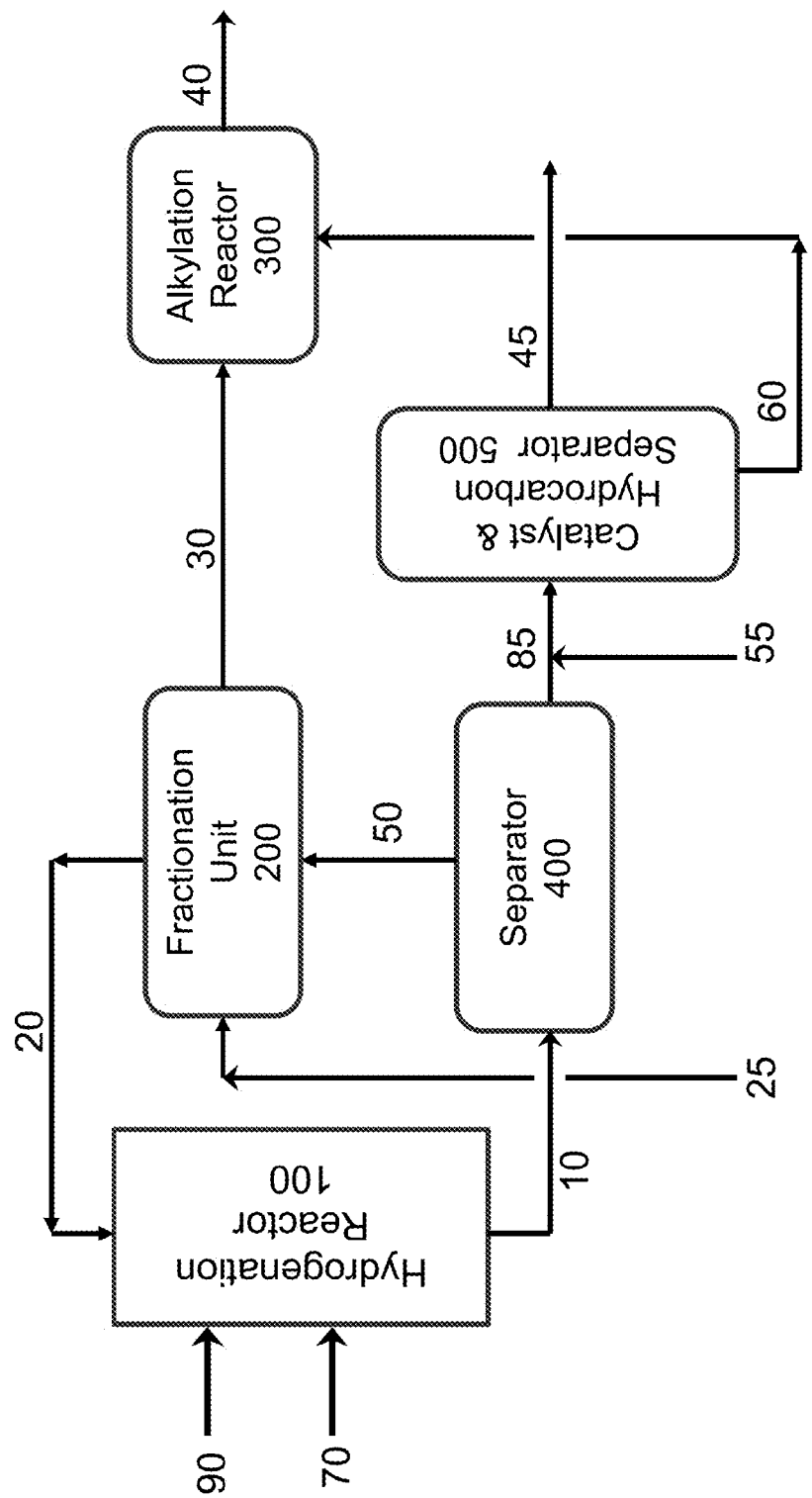
FIG. 4 is a diagram of a second alternative alkylation process unit with catalyst hydro-regeneration, hydrogen recycle and hydrogen chloride recovery.

FIG. 4 shows an alternative process wherein hydrogen is recycled and hydrogen chloride is recovered and recycled. In FIG. 4, hydrogen (90), and used catalyst (70) from an alkylation reactor (300) are fed to a hydrogenation reactor (100). The regenerated catalyst effluent (10) from the hydrogenation reactor (100) is fed to a separator (400), which separates the regenerated catalyst effluent (10) into an offgas (50) and a separated liquid (85). The offgas (50) is fed to a fractionation unit (200). A hydrocarbon extraction solvent (e.g., an isoparaffin feed to the alkylation reactor) is also fed to the fractionation unit (200). The fractionation unit (200) separates the offgas (50) into a gas fraction comprising the hydrogen gas (20) and a light hydrocarbon fraction comprising a hydrogen chloride (30). The gas fraction comprising the hydrogen gas (20) is recycled to the hydrogenation reactor (100). The light hydrocarbon fraction comprising the hydrogen chloride (30) is recovered and recycled to the alkylation reactor. The separated liquid (85) from the separator (400) is mixed with a conjunct polymer extraction solvent (55) and the mixture is fed to an ionic liquid catalyst and hydrocarbon separator (500). The ionic liquid catalyst and hydrocarbon separator (500) separates the mixture of the separated liquid (85) and conjunct polymer extraction solvent (55) into extracted conjunct polymer naphtha (45) and an ionic liquid catalyst stream (60). The extracted conjunct polymer naphtha (45) is sent to the refinery hydrocarbon pool of alkylate products (80). The ionic liquid catalyst stream is recycled to the alkylation reactor (300).

Figure 5:
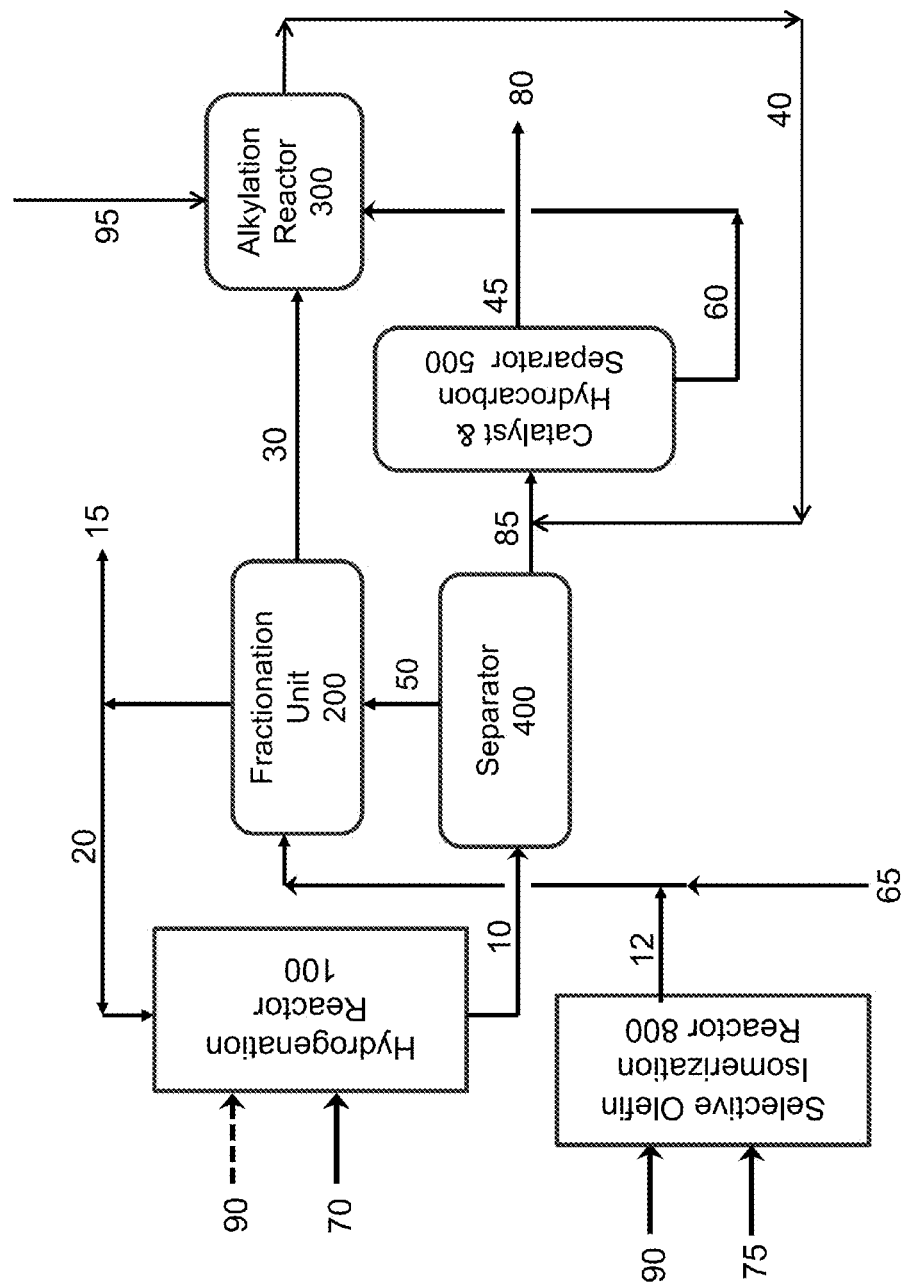
FIG. 5 is a diagram of a third alternative alkylation process unit with catalyst hydrogenation, hydrogen recycle and hydrogen chloride recovery. This diagram includes a selective olefin isomerization reactor.

FIG. 5 shows another alternative process wherein hydrogen is recycled and hydrogen chloride is recovered and recycled. In FIG. 5, a used catalyst (70) from an alkylation reactor (300) and optionally, hydrogen (90) are fed to a hydrogenation reactor (100). The regenerated catalyst effluent (10) from the hydrogenation reactor (100) is fed to a separator (400), which separates the regenerated catalyst effluent (10) into an offgas (50) and a separated liquid (85). In one embodiment, hydrogen (90) is not separately fed to the hydrogenation reactor (100), as all of the hydrogen needs for hydrogenation are supplied by a gas fraction comprising a hydrogen gas (20) from a fractionation unit (200). The offgas (50) is fed to the fractionation unit (200). Hydrogen (90) and an olefin feed (75) (e.g., 1-butene) are fed to a selective olefin isomerization reactor (800), wherein the olefin feed (75) is converted to isomerized olefins (12) (e.g., 2-butene). A hydrocarbon extraction solvent (25) (e.g., an isoparaffin feed (65) to be alkylated in the alkylation reactor) is mixed with the isomerized olefins (12) and the mixture is fed to the fractionation unit (200). The fractionation unit (200) fractionates the offgas (50) into a gas fraction comprising the hydrogen gas (20) and a light hydrocarbon fraction comprising a hydrogen chloride (30). The gas fraction comprising the hydrogen gas (20) is recycled to the hydrogenation reactor (100). Excess hydrogen and light hydrocarbons are removed in a recycle gas purge (15). The light hydrocarbon fraction comprising the hydrogen chloride (30) is recovered and recycled to the alkylation reactor. The separated liquid (85) from the separator (400) can be mixed with a conjunct polymer extraction solvent (55) or an effluent (40) from an alkylation reactor (300), (as shown), and the mixture is fed to an ionic liquid catalyst and hydrocarbon separator (500). The ionic liquid catalyst and hydrocarbon separator (500) separates the mixture of the separated liquid (85) and one or more of conjunct polymer extraction solvent (55) and effluent (40) from an alkylation reactor (300) into a stream comprised of extracted conjunct polymer naphtha (45) and an ionic liquid catalyst stream (60). The extracted conjunct polymer naphtha (45) is sent to the refinery hydrocarbon pool of alkylate products (80). The ionic liquid catalyst stream (60) is recycled to the alkylation reactor (300). As needed, chloride addition (95) can be made to the alkylation reactor (300).

Hydrogenation

The used catalyst is regenerated in the hydrogenation reactor. The hydrogenation reactor contacts the used catalyst with hydrogen and a hydrogenation catalyst to regenerate the ionic liquid catalyst. In one embodiment, zeolites or molecular sieves are added to the hydrogenation catalyst to improve the catalyst's performance. In one embodiment, the hydrogenation catalyst is supported. Typical support materials for the hydrogenation catalyst are kieselguhr, alumina, silica, and silica-alumina. Other support materials include alumina-boria, silica-alumina-magnesia, silica-alumina-titania and materials obtained by adding zeolites and other complex oxides thereto. When used, the support material has adequate mechanical strength and chemical stability at the hydrogenation reaction temperature.

In one embodiment, the hydrogenation is carried out in the presence of a catalyst which usually comprises a metal or non metal hydrogenation component on a porous support material, such as a natural clay or a synthetic oxide. Examples of metal hydrogenation components that can be used are Fe, Co, Ni, Ru, Rh, Pd, Pt, Ir, Os, Cr, Mn, Ti, V, Zr, Mo, W, and mixtures thereof. Examples of non metal hydrogenation components are Te, As, and mixtures thereof. The hydrogenation components can be used singly or in combination.

The hydrogenation can be carried out over a broad range of hydrogen pressures, typically from about 50 to 5,000 psig. Hydrogenation conditions can include temperatures of $-20°$ C. to $400°$ C., or $50°$ C. to $300°$ C.; and total pressures of atmospheric to 5,000 psig, or 50 to 2,500 psig. Hydrogenation contact times can be from 0.1 minute to 24 hours, such as 10 minutes to 12 hours. Feed to catalyst ratios during the hydrogenation can vary from 0.1 to 10 vol/vol/hour. A normal hydrocarbon can optionally be used as a solvent in the hydrogenation reactor.

Examples of hydrogenation of ionic liquid catalysts for regeneration, for example, are given in U.S. Pat. No. 7,691,771, U.S. Pat. No. 7,651,970, U.S. Pat. No. 7,678,727, and U.S. Pat. No. 7,825,055.

Separator for Regenerated Catalyst Effluent

In one embodiment, the separator (400) separates the regenerated catalyst effluent streams for efficient downstream processing. The separator can be configured in several different ways. For example, in FIG. 1, the separator separates the ionic liquid catalyst stream (60) from the regenerated catalyst effluent first. Then the offgas (50) stream containing hydrogen, hydrogen chloride, and hydrocarbon is sent to a fractionation unit (200) for further separation into a gas fraction comprising a hydrogen gas (20) and a light hydrocarbon fraction comprising a hydrogen chloride (30). In FIGS. 2, 4, and 5, the separator separates the regenerated catalyst effluent streams into an offgas (50) comprising hydrogen chloride gas and into a separated liquid (85). In FIG. 3, a hydrocarbon extraction solvent (25) was added to the separator to facilitate extraction of hydrogen chloride into a liquid stream. The separator (400) produces a gas fraction comprising a hydrogen gas (20), having a reduced level of hydrogen chloride, and a separated liquid (85). The separated liquid (85), comprising hydrogen chloride, hydrocarbon and ionic liquid catalyst, is sent to an ionic liquid catalyst and hydrocarbon separator (500).

Hydrocarbon Extraction Solvent

In one embodiment, the hydrogen chloride is extracted from the offgas of the hydrogenation reactor using a hydrocarbon extraction solvent. The hydrogen chloride can be extracted into the hydrocarbon extraction solvent, which is transmitted to the alkylation reactor. This embodiment is shown in FIGS. 3 through 5. The hydrocarbon extraction solvent can be any hydrocarbon that can serve as a solvent or reactant for the alkylation process. Examples of suitable extraction solvents for alkylation processes making alkylate gasoline are isobutane, alkylate gasoline, isomerized olefin, and mixtures thereof.

In one embodiment the hydrocarbon extraction solvent comprises an isomerized olefin. An example of an isomerized olefin is 2-butene. Processes for isomerizing olefins to make alkylate gasoline with improved RON are taught in U.S. Pat. No. 7,553,999.

In one embodiment, the hydrocarbon extraction solvent (25) is added to the hydrogenation reactor (100). In another embodiment, the hydrocarbon extraction solvent (25) is added to the regenerated catalyst effluent (10). In yet another embodiment, the hydrocarbon extraction solvent is added to either the separator (400) or the fractionation unit (200). In one embodiment, the hydrocarbon extraction solvent is fed into a stream selected from a regenerated catalyst effluent (10), an offgas (50) from a separator, or a combination thereof.

In FIG. 3, for example, the hydrocarbon extraction solvent is added to the regenerated catalyst effluent (10) either in the separator or prior to separating. In one embodiment, the effluent from the hydrogenation reactor can be separated by a series of a gas/liquid separator, a liquid/liquid separator, and a fractionation unit that is a distillation column. In one embodiment, the effluent from the hydrogenation reactor (100) is separated by the gas/liquid separator into: a) a gas fraction comprising a hydrogen gas (20) and b) separated liquid (85). The separated liquid comprises a light hydrocarbon fraction comprising a hydrogen chloride (30). In one embodiment, the liquid/liquid separator removes one liquid (regenerated alkylation catalyst), which is recycled back to an alkylation reactor, from a second liquid comprising the hydrocarbon extraction solvent and hydrogen chloride. The second liquid can be distilled in a fractionation unit into at least two streams, one being a portion of the light hydrocarbon fraction comprising the hydrogen chloride and the hydrocarbon extraction solvent, and the other being extracted conjunct polymer naphtha. In this example, the hydrocarbon extraction solvent can also be a reactant in the alkylation reactor. In this example, the hydrocarbon extraction solvent can be used to cool the effluent from the hydrogenation reactor.

The separating of the hydrogen gas and hydrogen chloride can be performed in a fractionation unit that is a distillation column. For example, in FIG. 5, the hydrocarbon extraction solvent comprises an isoparaffin (e.g., isobutane) and isomerized olefin. In this example, the hydrocarbon extraction solvent is mixed with the offgas from the hydrogenation reactor in the fractionation unit, e.g., a distillation column. In one embodiment, the isoparaffin and isomerized olefin are fed to the fractionation unit, used for the separating, at a location above where the offgas of the hydrogenation reactor is fed into the fractionation unit. In other words, the hydrocarbon extraction solvent is fed to the fractionation unit at a location above where the hydrogen gas and the hydrogen chloride are fed to the fractionation unit. In one embodiment, the hydrocarbon extraction solvent is fed to the fractionation unit in a counter current to the flow of offgas into the fractionation unit. In this example, and other embodiments, the hydrocarbon extraction solvent comprises an olefin and an isoparaffin. The olefin and the isoparaffin can be alkylated to make an alkylate gasoline blending component. In some embodiments, the alkylation catalyst is a chloroaluminate ionic liquid catalyst.

In one embodiment, the hydrocarbon extraction solvent comprising an olefin and an isoparaffin to be alkylated to make alkylate gasoline has an amount of isomerized olefin that is greater than 30 wt %, greater than 40 wt %, greater than 50 wt %, greater than 60 wt %, or greater than 70 wt % of the olefin in the hydrocarbon extraction solvent. For example, to make high RON alkylate gasoline blending component the olefin is greater than 10 wt %, greater than 15 wt %, greater than 30 wt %, greater than 40 wt %, greater than 50 wt %, and up to 100 wt % 2-butene, and the isoparaffin is isobutane.

In one embodiment, the hydrocarbon extraction solvent is fed at a vol/vol ratio of the hydrocarbon extraction solvent to the ionic liquid catalyst from 0.5 to 20.0, from 1.0 to 10.0, or from 1.5 to 5.0. The vol/vol ratio can be selected to provide the desired level of hydrogen chloride in the gas fraction comprising a (20). The desired level of hydrogen chloride in the gas fraction comprising the hydrogen can be any level at least 25 wt % lower than a level of hydrogen chloride in the regenerated catalyst effluent or offgas (50), such as less than 1,000 wppm, less than 600 wppm, 500 wppm or less, less than 200 wppm, or less than 100 wppm. Alternatively, the vol/vol ratio can be selected to provide the desired wt % of the hydrogen chloride produced in the hydrogenation reactor that is recovered and recycled to the alkylation reactor. In some embodiments the desired level of hydrogen chloride in the gas fraction comprising the hydrogen is much reduced, such as at least 50 wt % up to 99% reduced.

Reactants

In one embodiment, the at least the amount of the light hydrocarbon fraction comprising the hydrogen chloride (30) additionally comprises an isoparaffin and an olefin. This embodiment is shown, for example, in FIG. 5, where the isoparaffin (e.g., isoparaffin feed (65)) and the olefin (e.g., isomerized olefins (12)) can be hydrocarbon reactants for use in the alkylation reactor. The reactants to be alkylated, for example, can be an olefin and an isoparaffin or an olefin and an aromatic. In one example, the reactants comprise $C_2$ to $C_{20}$ olefins and $C_4$-$C_{20}$ isoparaffins. In one embodiment, the olefin comprises an isomerized olefin (e.g., 2-butene) and the isoparaffin comprises isobutane.

Recycling of the Light Hydrocarbon Fraction Comprising Hydrogen Chloride

In one embodiment, the at least the amount of the light hydrocarbon fraction comprising a hydrogen chloride that is recovered is not pre-treated, other than optional separating, before recycling to the alkylation reactor. For example, the process can use no pre-treating system, such as aqueous caustic, to remove excess hydrogen chloride from the light hydrocarbon fraction. By avoiding the use of any aqueous treating in the process, high amounts of the hydrogen chloride can be recycled and additional drying of the feeds to the alkylation reactor is greatly reduced or eliminated.

In one embodiment, the at least the amount of the light hydrocarbon fraction is not dried before recycling to the hydrogenation reactor. Again, this is possible, because the process does not require any aqueous steps to remove the hydrogen chloride. This is an advantage over the process disclosed in FIG. 2, where the hydrogen chloride is removed using an aqueous caustic wash, and the recycled hydrogen from the hydrogen chloride removal step is wet and must be thoroughly dried before recycling to the hydro-regeneration reactor. If the recycled hydrogen were not dried, it would react violently with the ionic liquid catalyst, destroy the catalyst, and potentially pose an explosion hazard.

Conjunct Polymer Extraction Solvent

In one embodiment, a conjunct polymer extraction solvent (55), for example an isoparaffin feed is blended with a separated liquid (85) from the separator (400). The conjunct polymer extraction solvent can be a hydrocarbon reactant, a light hydrocarbon solvent, an alkylate gasoline, or mixtures thereof. An example of this is shown in FIG. 4.

Chloride Retention

In one embodiment, at least 80 wt % of the hydrogen chloride produced in the hydrogenation reactor is recovered and recycled to the alkylation reactor. For example, at least 85 wt %, at least 90 wt %, at least 94 wt %, up to 98 wt % of the hydrogen chloride can be recycled. In one embodiment, the chloride in the used catalyst is a hydrogen chloride co-catalyst.

By recycling the chloride, the amount of the chloride that needs to be added to the process is greatly reduced. Examples of chloride that may be added to the process to maintain the ionic liquid catalyst activity include hydrogen chloride, alkyl chloride, and metal chloride. In one example, the chloride added to the process is n-butyl chloride or t-butyl chloride. The chloride added to the process can be added at any point in the process, but is usually introduced into the alkylation reactor (300) as either a separate stream, or can be mixed with the ionic liquid catalyst stream (60) or the light hydrocarbon fraction comprising the hydrogen chloride (30).

Hydrogen Recycling

The hydrogen gas is separated and recycled to the hydrogenation reactor. Recycling the hydrogen can save significant cost associated with hydrogen supply. In one embodiment, the process additionally comprises removing a recycle gas purge (15) from the effluent from the fractionation unit (200). In one embodiment, the recycle gas purge (15) comprises an excess of the hydrogen gas from the offgas (50) of the hydrogenation reactor. This is demonstrated in FIG. 5. The excess hydrogen from the recycle gas purge (15) can then be utilized in other parts of an integrated refinery, stored, or used for other purposes. The removal of the excess hydrogen gas can eliminate concerns over excessive hydrogen in distillation column overhead systems.

In one embodiment, the process comprises compressing the recycled hydrogen gas in the gas fraction comprising the hydrogen gas (20) before recycling it to the hydrogenation reactor (100). The compression, when used, can use conventional compressor equipment and piping because the gas fraction comprising a hydrogen gas contains limited amounts of hydrogen chloride, and is thus not highly corrosive.

Separating

In one embodiment, the separating of the hydrogen gas and the hydrogen chloride from the offgas is done in a distillation column. In another embodiment, reactants to be alkylated in the alkylation reactor are also fed into the distillation column used to separate the hydrogen gas and the hydrogen chloride. This embodiment is shown in FIG. 4. The reactants can be fed either as a mixture or separately into the distillation column.

In one embodiment, the reactants are fed to the distillation column at one or more locations above where the at least the part of the gas fraction is fed to the distillation column. In one embodiment, wherein the separating is done in a distillation column into which is fed reactants to be alkylated, the reactants can be fed to the distillation column at a location above where the offgas from the hydrogenation reactor is fed to the distillation column. In one embodiment, the reactants to be alkylated, e.g., makeup isobutane and isomerized olefins are fed either separately or combined into the distillation column.

In one embodiment, as shown in FIG. 5, the regenerated catalyst effluent (10) out of the hydrogenation reactor (100) is first separated by a gas/liquid separator (400) into an offgas (50) gas stream comprising hydrogen and hydrogen chloride and a separated liquid (85) stream. The separated liquid (85) is fed to a catalyst and hydrocarbon separator (500) where it is further separated into an ionic liquid catalyst stream (60) and extracted conjunct polymer naphtha (45). The offgas (50) is mixed with an isoparaffin feed (65) comprising isobutane and with isomerized olefins (12) (e.g., 2-butene) in a fractionation unit (200), where they are distilled into a gas fraction comprising a hydrogen gas (20), and a light hydrocarbon fraction comprising a hydrogen chloride (30). The light hydrocarbon fraction comprising a hydrogen chloride (30) additionally comprises the isoparaffin (e.g., isobutane), the isomerized olefins (e.g., 2-butene), and the hydrogen chloride, and this light hydrocarbon fraction is recycled to the alkylation reactor.

In one embodiment, the stream comprising the hydrogen chloride from the distillation column is mixed with a recycled stream comprising a mixture of a second hydrogen chloride and a propane, from the alkylation reactor, before recycling the mixture back into the alkylation reactor.

In one embodiment, the light hydrocarbon fraction comprising the hydrogen chloride from the distillation column also comprises isobutane and olefins. This light hydrocarbon fraction can be mixed with a recycled stream from the ionic liquid reactor before recycling the mixture back into the alkylation reactor. The recycled stream from the ionic liquid reactor can, for example, comprise hydrogen chloride, propane, and isobutane.

Regenerated Catalyst Effluent

The regenerated catalyst effluent (10) can comprise regenerated ionic liquid catalyst having increased catalytic activity compared to the used catalyst before hydrogenation. In one embodiment, the regenerated catalyst effluent comprises a regenerated ionic liquid catalyst that is eventually recycled to the alkylation reactor. This embodiment is shown in all the figures. The regenerated catalyst effluent (10) also comprises at least the portion that is separated into the gas fraction comprising a hydrogen gas (20) and the light hydrocarbon fraction comprising a hydrogen chloride (30).

In one embodiment, see FIG. 3 for example, the regenerated catalyst effluent (10) is separated in a gas/liquid separator (400) to produce the gas fraction comprising the hydrogen gas (20) and a separated liquid (85) that comprises hydrogen chloride. The gas fraction comprising the hydrogen gas (20) is recycled from the gas/liquid separator (400) to the hydrogenation reactor (100). The separated liquid (85) comprising the hydrogen chloride can be separated in an ionic liquid catalyst and hydrocarbon separator (500) to produce two streams, one comprising the ionic liquid catalyst stream (60) having regenerated catalyst and a hydrocarbon stream (52) comprising one or more reactants for alkylation, extracted conjunct polymer naphtha (45), and the hydrogen chloride. The hydrocarbon stream (52) can be separated in a fractionation unit (200) (e.g., a distillation column) to produce the light hydrocarbon fraction comprising a hydrogen chloride (30) and one or more reactants for alkylation and a heavier or bottom cut comprising extracted conjunct polymer naphtha (45). The light hydrocarbon fraction comprising the hydrocarbon reactants and the hydrogen chloride is recycled to the alkylation reactor (300) and the heavier or bottom cut is mixed with the alkylate products (80), e.g., alkylate gasoline.

Ionic Liquid Catalyst

The ionic liquid catalyst can be any ionic liquid which works well with a chloride as a co-catalyst. The ionic liquid catalyst is an organic salt or mixture of salts. The ionic liquid catalyst can be characterized by the general formula Q+A−, wherein Q+ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, alkyl-aryl sulfonate, and benzene sulfonate (e.g., 3-sulfurtrioxyphenyl). In one embodiment the ionic liquid catalyst is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl-substituted-pyridinium halide compounds for example 1-butylpyridinium halide, benzylpyridinium halide, or hydrocarbyl-substituted-imidazolium halides, such as for example, 1-ethyl-3-methylimidazolium chloride.

In one embodiment, the ionic liquid catalyst is an organic salt that is hygroscopic in nature and has a tendency to attract and hold water molecules from the surrounding environment. With these ionic liquid catalysts, in order to maintain the integrity of the ionic liquid catalyst and its catalytic performance, the organic salts from which the ionic liquid catalyst is synthesized, are thoroughly dried before the catalyst synthesis, and moisture-free conditions are maintained during the alkylation reaction.

In one embodiment the ionic liquid catalyst is selected from the group consisting of hydrocarbyl-substituted-pyridinium chloroaluminate, hydrocarbyl-substituted-imidazolium chloroaluminate, quaternary amine chloroaluminate, trialkyl amine hydrogen chloride chloroaluminate, alkyl pyridine hydrogen chloride chloroaluminate, and mixtures thereof. For example, the used ionic liquid catalyst can be an acidic haloaluminate ionic liquid, such as an alkyl substituted pyridinium chloroaluminate or an alkyl substituted imidazolium chloroaluminate of the general formulas A and B, respectively.

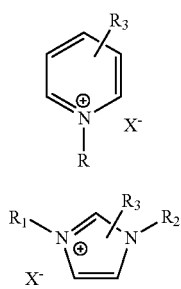

In the formulas A and B; R, $R_1$, $R_2$, and $R_3$ are H, methyl, ethyl, propyl, butyl, pentyl or hexyl group, X is a chloroaluminate. In another embodiment, R, $R_1$, $R_2$, and $R_3$ are methyl, ethyl, propyl, butyl, pentyl or hexyl group, and X is a chloroaluminate. In one embodiment the X is $AlCl_4^-$, $Al_2Cl_7^-$, or $Al_3Cl_{10}^-$. In the formulas A and B, R, $R_1$, $R_2$, and $R_3$ may or may not be the same. In one embodiment the ionic liquid catalyst is N-butylpyridinium heptachlorodialuminate [$Al_2Cl_7^-$]. In one embodiment the ionic liquid catalyst is 1-Ethyl-3-methylimidazolium tetrachloroaluminate [emim$^+$] [$AlCl_4^-$].

Products

Alkylate products that can be produced by this process include alkylated aromatics and alkylated isoparaffins. The alkylate products can have a broad range of uses including, for example, as gasoline blending components, middle distillates, base oils, and petrochemical components. The gasoline blending components can have excellent properties, including high RONs and low RVP. The base oils can have excellent properties, including low pour points, low cloud points, and varied viscosity indexes and kinematic viscosities. The middle distillates can have unique branching properties, making some of them even suitable as jet fuel. Processes for making high quality alkylate gasoline blending components are described, for example, in earlier patent publications, including U.S. Pat. No. 7,432,408, U.S. Pat. No. 7,432,409, U.S. Pat. No. 7,553,999, U.S. Pat. No. 7,732,363, and US20110230692. Processes for making base oils are described, for example, in U.S. Pat. No. 7,569,740, U.S. Pat. No. 7,576,252, U.S. Pat. No. 8,124,821, U.S. Pat. No. 8,101,809, and patent application Ser. No. 12/966,638 (filed Dec. 13, 2010) and Ser. No. 12/966,738 (filed Dec. 13, 2010). Processes for making middle distillates are described, for example, in U.S. Pat. No. 7,923,593, U.S. Pat. No. 7,919,664, U.S. Pat. No. 7,955,495, and U.S. Pat. No. 7,923,594. Alkylated aromatic products and processes are described in U.S. Pat. No. 7,732,651.

In one embodiment the effluent (40) from the alkylation reactor comprises the alkylate products (80). In one embodiment, a propane product, an n-butane product, and an alkylate gasoline blending component product are separated from an effluent from the alkylation reactor.

Extracted Conjunct Polymer Naphtha

In one embodiment, the process additionally comprises separating an extracted conjunct polymer naphtha (45) from an effluent from the hydrogenation reactor and blending the extracted conjunct polymer naphtha into an alkylate gasoline. The extraction of the extracted conjunct polymer naphtha (45) can be performed in a catalyst & hydrocarbon separator (500) or in a fractionation unit (200). The hydrogenation of the conjunct polymer can improve the properties of the conjunct polymer made during the alkylation reaction such that it has a suitable boiling range and purity to be blended into high quality alkylate gasoline. Blending the extracted conjunct polymer naphtha (45) in this way can greatly reduce waste disposal and equipment costs. For example, incineration, neutralization, and storage equipment can be eliminated from the alkylation process unit.

The extracted conjunct polymer naphtha (45) from the offgas of the hydrogenation reactor can have a final boiling point less than 246° C. (475° F.), such as having a boiling range distribution from 90° F. to 474° F. (32° C. to 246° C.), from 95° F. to 460° F. (35° C. to 238° C.), from 100° F. to 450° F. (38 C to 232° C.), from 105° F. to 445° F. (41° C. to 229° C.), or from 110° F. to 440° F. (43° C. to 227° C.). The test method used for determining the boiling range distribution is ASTM D86-11b. In addition, the extracted conjunct polymer naphtha can have a low sulfur content (e.g., from 0.05 wt % to 0.5 wt %) a low bromine number (e.g., from <1 to 5), and a low chloride content (e.g., from 5 ppm to 500 ppm), even without additional treatment.

In one embodiment, the process produces unique alkylate gasoline products that comprise the extracted conjunct polymer naphtha (45) that has been hydrogenated and extracted from the regenerated catalyst effluent (10). In one embodiment, the alkylate gasoline comprises the extracted conjunct polymer naphtha (45) having a boiling point less than 246° C. (475° F.), and as further described above, extracted from the used catalyst (70).

Alkylation Process Unit

The alkylation process unit is one designed to conduct the processes described herein. Process units performing these processes are shown in FIGS. 1, 3, 4, and 5. In one embodiment, the process unit comprises a hydrogenation reactor, a fractionation unit fluidly connected to the hydrogenation reactor, a first connection between the fractionation unit and the hydrogenation reactor for transmitting at least a part of the gas fraction comprising a hydrogen gas to the hydrogenation reactor, and a second connection between the fractionation unit and the alkylation reactor to transmit at least a amount of the light hydrocarbon fraction comprising a hydrogen chloride to the alkylation reactor. By "fluidly connected" it is meant that the connection provides a conduit wherein the contents move freely past one another and have the tendency to assume the shape of their container; a liquid or gas. In another embodiment, the process unit comprises: a) a hydrogenation reactor, wherein a used catalyst comprising an ionic liquid catalyst and a chloride produces a regenerated catalyst effluent; b) a separator, fluidly connected to the hydrogenation reactor and a fractionation unit; wherein the separator separates the regenerated catalyst effluent into a gas fraction comprising a hydrogen gas and into a separated liquid; and wherein the fractionation unit separates a hydrocarbon stream from the separated liquid into a light hydrocarbon fraction comprising a hydrogen chloride and an extracted conjunct polymer naphtha; c) a first connection between the separator and the hydrogenation reactor for transmitting at least a part of the gas fraction to the hydrogenation reactor; and d) a second connection between the fractionation unit and an alkylation reactor to transmit at least an amount of the light hydrocarbon fraction to the alkylation reactor.

In one embodiment, the alkylation process unit additionally comprises a third connection between a product treatment unit and the second connection wherein the light hydrocarbon fraction is mixed with a recycled stream from the product treatment unit comprising a mixture of a light hydrogen chloride and a propane. In one embodiment, the alkylation process unit additionally comprises a selective olefin isomerization reactor, fluidly connected to the fractionation unit, which produces isomerized olefins that are fed to the fractionation unit.

In one embodiment, as shown in FIGS. 4 and 5, the alkylation process unit comprises a separator between the hydrogenation reactor and the fractionation unit, fluidly connected to the hydrogenation reactor and the alkylation reactor; wherein the separator separates a separated liquid (85) that comprises a regenerated ionic liquid catalyst and an extracted conjunct polymer naphtha from an offgas (50) comprising the hydrogen gas and the hydrogen chloride. In another embodiment, the alkylation process unit additionally comprises one or more separators between the hydrogenation reactor and the fractionation unit, fluidly connected to the hydrogenation reactor and the alkylation reactor; wherein the one or more separators produce an offgas that is fed to the fractionation unit and also produce an ionic liquid catalyst stream that is fed to the alkylation reactor.

In one embodiment, the alkylation process unit additionally comprises a compressor located before the hydrogenation reactor (100), that compresses the at least the part of the gas fraction comprising the hydrogen gas (20) before recycling the at least the part of the gas fraction to the hydrogenation reactor (100). In another embodiment, the alkylation process unit additionally comprises a compressor between the fractionation unit (200) and the hydrogenation reactor (100). A compressor is a mechanical device that increases the pressure of a gas by reducing its volume. Examples of types of compressors are hermetically sealed, open, or semi-hermetic, centrifugal, diagonal, mixed-flow, axial-flow, reciprocating, rotary screw, rotary vane, scroll, diaphragm, and air bubble.

In one embodiment, the alkylation process unit additionally comprises a third connection between a product treatment unit and the second connection, wherein the light hydrocarbon fraction comprising a hydrogen chloride (30) is mixed with a recycled stream, from the product treatment unit, comprising a mixture of a gaseous hydrogen chloride and a propane. The product treatment unit is used to separate and refine the products produced by the process and may include further hydrotreatment and separation steps.

The fractionation unit (200) can be fluidly connected directly to the hydrogenation reactor (100) or indirectly via an additional separation unit, such as a gas/liquid separation unit. An example of a liquid/liquid separator that can be used is an ionic liquid catalyst and hydrocarbon separator (500), is shown in FIGS. 3, 4, and 5.

EXAMPLES

Example 1

Ionic Liquid Catalyst Comprising Anhydrous Metal Halide

Various ionic liquid catalysts made of metal halides such as $AlCl_3$, $AlBr_3$, $GaCl_3$, $GaBr_3$, $InCl_3$, and $InBr_3$ could be used for the catalytic processes. N-butylpyridinium chloroaluminate ($C_5H_5C_4H_9Al_2Cl_7$) ionic liquid catalyst is an example used in our process.

The catalyst has the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Example 2

Alkylation of $C_4$ Olefin and Isobutane to Make Alkylate Gasoline with and without HCl Recycle Evaluation of $C_4$ olefins alkylation with isobutane was performed in a continuously stirred tank reactor using typical refinery mixed $C_4$ olefin feed and isobutane. An 8:1 molar mixture of isobutane and olefin was fed to the reactor while vigorously stirring. An ionic liquid catalyst was fed to the reactor via a second inlet port targeting to occupy 6 vol % in the reactor. A small amount of n-butyl chloride was added to produce anhydrous HCl gas. The average residence time (combined volume of feeds and catalyst) was about 4 minutes. The outlet pressure was maintained at 200 psig and the reactor temperature was maintained at 95° F. (35° C.) using external cooling.

The reactor effluent was separated with a gravity separator into a hydrocarbon phase and an ionic liquid catalyst phase. The hydrocarbon stream was further separated into multiple streams: a $C_3^-$ stream containing HCl, an $nC_4$ stream, an $iC_4$ stream and an alkylate gasoline stream. The alkylate product had 94 Research Octane Number and 410° F. (210° C.) end point. When the $C_3^-$ stream containing HCl was recycled to the alkylation reactor, we were able to lower the n-butyl chloride usage by 10% without affecting alkylate gasoline properties. This confirmed that recovering HCl with light hydrocarbon is an effective way to capture HCl and reuse.

Example 3

Isomerization of Olefin Feed, Alkylation, Regeneration of Ionic Liquid Catalyst by Hydrogenation and a Composition of Hydrogenation Reactor Offgas A refinery $C_3$ and $C_4$ olefin stream from a Fluid Catalytic Cracking Unit (FCC unit) was isomerized with a $Pd/Al_2O_3$ catalyst at 66° C. (150° F.) and 250 psig in the presence of hydrogen to produce an isomerized $C_3$ and $C_4$ olefin feed with the composition shown in Table 1.

TABLE 1

| Composition of Olefin Feed | |
|---|---|
| Composition | Mol % |
| Propane, C3 | 13.3 |
| Propylene, C3= | 25.4 |
| 1-Butene, 1-C4= | 2.3 |
| 2-Butene, 2-C4= | 16.2 |
| Isobutylene, i-C4= | 6.7 |
| n-Butane, nC4 | 12.4 |
| Isobutane, iC4 | 22.2 |
| C5+ | 1.6 |
| Sum | 100.0 |

The isomerized olefin was alkylated with isobutane in a continuously stirred tank reactor. An 8:1 molar mixture of isobutane and olefin was fed to the reactor while vigorously stirring. An ionic liquid catalyst was fed to the reactor via a second inlet port targeting to occupy 6 vol % in the reactor. A small amount of n-butyl chloride was added to produce anhydrous HCl gas. The average residence time (combined volume of feeds and catalyst) was about 4 minutes. The outlet pressure was maintained at 200 psig and the reactor temperature was maintained at 95° F. (35° C.) using external cooling. The alkylation reactor effluent was separated to a hydrocarbon stream and an ionic liquid catalyst stream. The ionic liquid catalyst was recycled back to the alkylation reactor and the conjunct polymer level of the ionic liquid catalyst was gradually increased.

Figure 6:
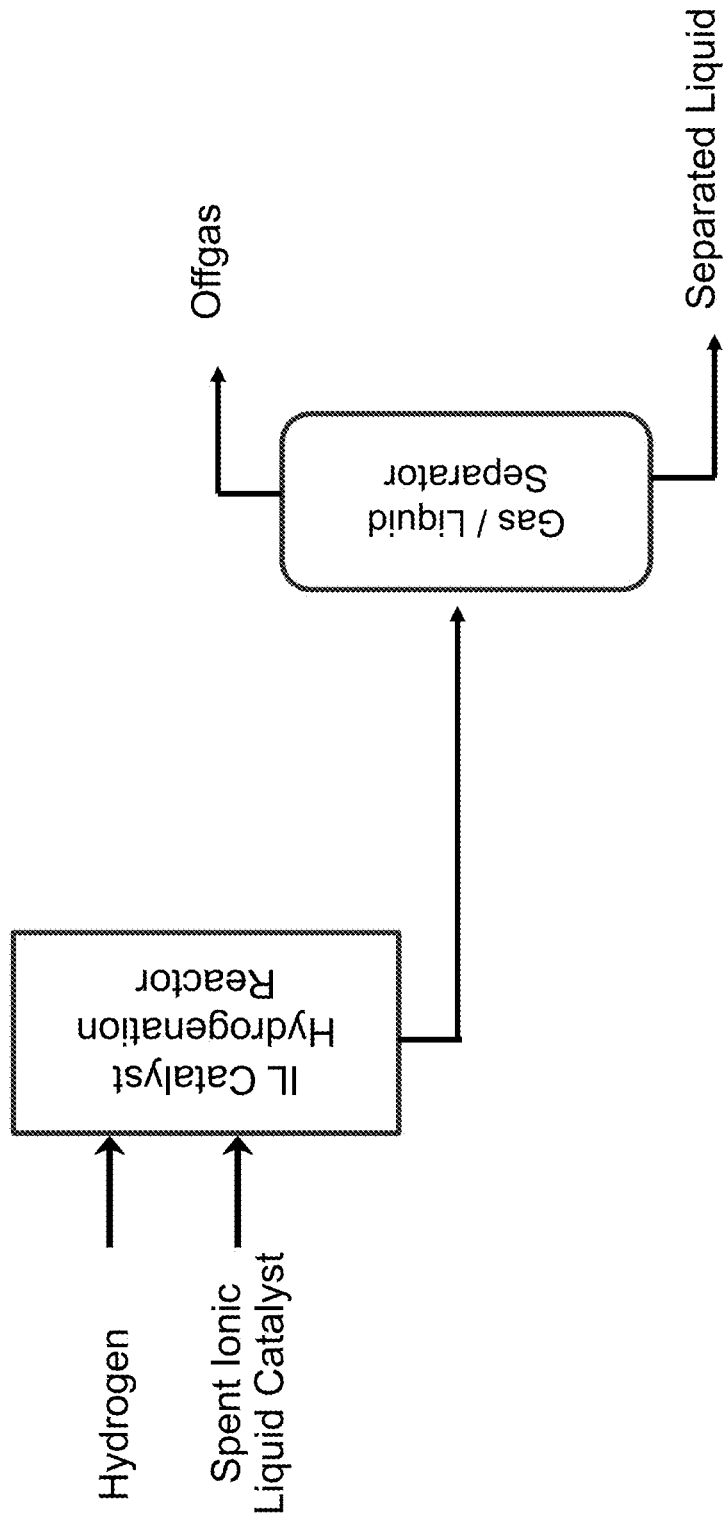
FIG. 6 is a diagram of a hydro-regeneration process without hydrocarbon extraction solvent.

Used ionic liquid catalyst containing 5 wt % conjunct polymer was regenerated by passing the ionic liquid catalyst through a hydrogenation reactor under $H_2$ atmosphere. 100% pure hydrogen gas was used. Hydro-regeneration of the ionic liquid catalyst was operated at 350° F. (177° C.), 350 psig, 5000 scf $H_2$/bbl ionic liquid catalyst, and 0.2 linear hourly space velocity (LHSV) in the presence of a hydrogenation catalyst containing Pt and Pd. The hydrogenation reactor effluent was separated into offgas and separated liquid streams in a gas/liquid separator as shown in FIG. 6. The separated liquid comprised regenerated ionic liquid catalyst and extracted conjunct polymer naphtha. At these conditions, 80 wt % of the conjunct polymer in the ionic liquid catalyst was converted to light material and the regenerated ionic liquid catalyst contained 1% conjunct polymer. The hydrogenation reactor offgas from the gas-liquid separation unit contained mostly $H_2$ and 6000 ppm of HCl. The offgas also contained 95% $H_2$ and 5 vol % of $C_3$-$C_6$ light hydrocarbons, while the bulk of light hydrocarbon was propane and isobutane. The purity of the hydrogen gas was dropped from 100% to 95% in one pass. In order to recycle the hydrogenation reactor offgas back to the hydrogenation unit, HCl and light hydrocarbon needed to be removed.

This example clearly shows that it will be highly desirable to have an efficient way to remove and reuse the HCl and hydrocarbon in the offgas. By removing the HCl and hydrocarbon in the offgas, the hydrogen gas can be recycled back to the hydrogenation reactor for repeated use. For removal of hydrogen chloride, a caustic treating method as shown in FIG. 2, would result in substantial loss of HCl and light hydrocarbon.

The separated liquid stream from the hydrogenation unit was further separated into the extracted conjunct polymer naphtha and regenerated ionic liquid catalyst. The regenerated ionic liquid catalyst was recycled back to the alkylation reactor for reuse.

Example 4

Improved HCl Recovery from Ionic Liquid Catalyst Hydrogenation with Hydrocarbon Extraction Solvent Used ionic liquid catalyst containing 4 wt % conjunct polymer from a alkylation reactor was regenerated by passing the ionic liquid catalyst through a hydrogenation reactor under $H_2$ atmosphere. 100% pure hydrogen gas was fed to the hydrogenation reactor. The hydrogenation reactor was operated at 350° F. (177° C.), 400 psig, 1500 scf $H_2$/bbl ionic liquid catalyst, and 2.0 LHSV in the presence of a hydrogenation catalyst containing Pt and Pd. The hydrogenation reactor effluent was separated into gas and liquid streams as shown in FIGS. 3 and 6. At these conditions, 25 wt % of the conjunct polymer in the ionic liquid catalyst was converted to light hydrocarbon material, and the regenerated ionic liquid catalyst contained 3 wt % conjunct polymer. The hydrogenation reactor offgas from the gas-liquid separator contained mostly $H_2$ and 1500 ppm of HCl. The offgas also contained 93 vol % $H_2$ and 7 vol % of $C_3$-$C_6$ light hydrocarbons, while about 85-90 vol % of the light hydrocarbon was propane and isobutane.

To demonstrate the concept of HCl extraction with hydrocarbon extraction solvent, n-hexane solvent was added to the hydrogenation reactor effluent at 2 and 4 times the volume of n-hexane to the ionic liquid catalyst flow. Then the mixture was further separated with the same separator. The analysis results of the offgas stream are summarized in Table 1 below.

TABLE 2

| HCl Content in Hydrogenation Offgas with Hydrocarbon Extraction Solvent | | | |
|---|---|---|---|
| n-Hexane Flow Rate | No n-Hexane Flow | 2.0 vol/vol n-Hexane/Ionic liquid flow to the Hydrogenation Reactor Effluent | 4.0 vol/vol n-Hexane/ Ionic liquid flow to the Hydrogenation Reactor Effluent |
| HCl, ppm | 1500 | 500 | 300 |
| H2 Purity, vol % | 93 | 94 | 95 |
| C3-C6, vol % | 7 | 6 | 5 |

As we added n-hexane solvent to the hydrogenation reactor effluent, the hydrogen chloride content in the offgas dropped from 1500 ppm to 300 ppm. These results clearly suggested that the hydrogen chloride in the offgas stream can be extracted by adding hydrocarbon extraction solvent. The above set-up was a simple single stage separator. The extraction of the hydrogen chloride will improve further with multistage separation extractor, and possibly with counter-current flows of the two feeds to the separator.

Example 5

An Integrated Process for $H_2$ Recycle and HCl Recovery from Ionic Liquid Catalyst Hydrogenation This example shows an efficient $H_2$ purification/HCl recovery process using the feeds to the alkylation reactor. One embodiment is shown in FIG. 5.

The offgas (50) separated from the regenerated catalyst effluent (10) from the hydrogenation reactor (100) was mixed with isomerized olefins (12) and isoparaffin feed (65) comprising make-up isobutane in the amounts as shown in Table 3. The combined mixture was separated in a fractionation unit (200) that was a distillation column to separate the mixture into a) a gas fraction comprising a hydrogen gas (20), having low hydrogen chloride content, and b) a light hydrocarbon fraction comprising a hydrogen chloride (30). The light hydrocarbon fraction comprising a hydrogen chloride (30) contained the bulk (>90 wt %) of hydrogen chloride generated by the hydrogenation of the used catalyst (70) (in this example, ionic liquid catalyst). The compositions of the hydrogen gas streams before and after the HCl extraction (i.e., Hydrogenation Unit Offgas [offgas (50)] and Purified Gas Stream [gas fraction comprising a hydrogen gas (20)], respectively) are shown in Table 3.

The gas fraction comprising a hydrogen gas (20) (also referred to as the purified hydrogen gas stream) was recycled back to the hydrogenation reactor (100) for regeneration of the used catalyst (70), in this case a used ionic liquid catalyst. The used ionic liquid catalyst containing 5 wt % conjunct polymer was passed through the hydrogenation reactor (100) at 350° F. (177° C.), 450 psig, 5000 scf $H_2$/bbl ionic liquid catalyst using recycled hydrogen gas, and 0.2 weight hourly space velocity (WHSV) in the presence of a hydrogenation catalyst containing Pt and Pd. At these conditions, 80 wt % of the conjunct polymer in the used ionic liquid catalyst was converted to light material and the regenerated ionic liquid catalyst contained 1% conjunct polymer. The hydrogenation reactor offgas [offgas (50)] from the gas-liquid separation unit [Separator (400)] contained 6000 ppm of HCl and substantial amounts of hydrogen and light hydrocarbon.

The separated liquid from the Example 3 was mixed with isobutane extraction solvent and then sent to another separator to produce an ionic liquid catalyst stream and a hydrocarbon stream containing conjunct polymer naphtha. The regenerated ionic liquid catalyst was sent back to the alkylation reactor. The hydrocarbon stream was sent to a stripper to remove the isobutane extraction solvent, and pure, extracted conjunct polymer naphtha (45) was recovered. The extracted conjunct polymer naphtha (45) was analyzed for its properties. The properties of the extracted conjunct polymer naphtha (45) are compared with alkylate gasoline in Table 4. Also,

TABLE 3

Composition of Recycle $H_2$ Stream and Alkylation Reactor Feed with Recovered HCl

| | Hydrogenation Unit Offgas (Offgas (50)) | Isomerized Olefins (12) | Make-Up Isobutane (Isoparaffin feed (65)) | Purified Gas Stream (Gas fraction comprising a hydrogen gas (20)) | HCl-Rich Hydrocarbon Feed (Light hydrocarbon fraction comprising a hydrogen chloride (30)) |
|---|---|---|---|---|---|
| Material Balance | | | | | |
| HCl, mole/day | 0.605 | 0 | 0 | 0.024 | 0.581 |
| $H_2$, mole/day | 76 | 6 | 0 | 82 | 0.02 |
| $C_3^=$, mole/day | 0 | 170 | 0 | 0.35 | 169 |
| $C_3$, mole/day | 12 | 74 | 44 | 16 | 113 |
| $C_4^=$, mole/day | 0 | 215 | 0 | 0 | 215 |
| $iC_4$, mole/day | 13 | 165 | 243 | 22 | 398 |
| $nC_4$, mole/day | 1 | 97 | 28 | 1 | 124 |
| HCl Concentration | | | | | |
| HCl Recovery, wt % | Source | — | — | 4% | 96% |
| HCl, ppm | 6000 | — | — | 200 | — |

The results in Table 3 show that 96% of the hydrogen chloride from the hydro-regeneration offgas [offgas (50)] was recovered by our integrated process using a hydrocarbon extraction solvent (25). The hydro-regeneration offgas [offgas (50)] had very high concentration of hydrogen chloride, 6000 ppm. After the fractionation, the Purified Gas Stream [(Gas fraction comprising a hydrogen gas (20)] contains only 200 ppm of HCl and the Purified Gas Stream was recycled to the hydrogenation reactor (100). This process also produced a desirable light hydrocarbon fraction comprising a hydrogen chloride (30), with little residual hydrogen, and the light hydrocarbon fraction comprising a hydrogen chloride (30) was sent to the alkylation reactor (300).

This example showed that maximum recovery of hydrogen chloride could be achieved with extensive use of hydrocarbon extraction solvent where both make-up isobutane and olefin alkylation feeds are used to extract hydrogen chloride from the hydrogenation offgas. The efficient recovery and recycle of hydrogen chloride greatly lowers the operating cost and reduces the quantity of make-up HCl that needs to be added to the process.

Example 6

Properties of Extracted Conjunct Polymer Naphtha and a Blend with Alkylate Gasoline Extracted conjunct polymer naphtha (45) produced by hydro-regeneration can be recovered and blended to alkylate gasoline, as shown in this example.

a blend of 0.2 vol % extracted conjunct polymer naphtha and 99.8% alkylate gasoline was prepared and its properties are summarized in Table 4, with the detailed composition shown in Table 5.

TABLE 4

Properties of Alkylate Gasoline, Conjunct Polymer Naphtha, and a Gasoline Blend Containing Alkylate and Conjunct Polymer Naphtha

| | | Alkylate Gasoline | 100% Extracted Conjunct Polymer Naphtha, As-Produced | Blend of Alkylate Gasoline with Conjunct Polymer Naphtha |
|---|---|---|---|---|
| D86 | IBP, ° F. | 108 | 114 | 108 |
| | 10%, ° F. | 168 | 185 | 169 |
| | 50%, ° F. | 213 | 241 | 213 |
| | 90%, ° F. | 281 | 297 | 283 |
| | End Point, ° F. | 396 | 439 | 401 |
| Bromine Number | | <1 | 1 | <1 |
| Research Octane Number (RON) | | 89 | 74 | 89 |
| Motor Octane Number (MON) | | 86 | 70 | 85 |

The extracted conjunct polymer naphtha had a boiling point end point of 439° F. and a 90 vol % boiling point of 297° F., indicating it is in the gasoline boiling range. The conjunct polymer naphtha was fully saturated in the hydrogenation reactor as shown by the Bromine Number of only 1. The Octane Numbers of the conjunct polymer naphtha are only slightly worse compared to pure alkylate gasoline, but the volume used in the blending is very small and does not affect the Octane Number (either RON or MON) significantly. The properties of the blend containing 0.2 vol % extracted conjunct polymer naphtha and alkylate gasoline showed little change from the pure alkylate gasoline, indicating that the extracted conjunct polymer naphtha can be successfully blended to make high quality alkylate gasoline, even with no additional post-treatment.

TABLE 5

Composition of Alkylate Gasoline, Conjunct Polymer Naphtha, and a Gasoline Blend Containing Alkylate and Conjunct Polymer Naphtha

| Alky Product Compostion, wt % | IL Alkylate | | Polymer Naphtha | | Blend | |
| --- | --- | --- | --- | --- | --- | --- |
| Total C4 | 0.9 | 0.9 | 1.8 | 1.8 | 1.0 | 1.0 |
| Total C5 | 8.0 | 8.0 | 6.2 | 6.2 | 8.2 | 8.2 |
| 2,2-Dimethylbutane | 0.0 | | 0.2 | | 0.0 | |
| 2,3-Dimethylbutane | 4.4 | | 1.0 | | 4.3 | |
| C6 Other | 2.1 | | 12.9 | | 2.1 | |
| Total C6 | | 6.5 | | 14.1 | | 6.5 |
| 2,3-Dimethylpentane | 11.9 | | 0.8 | | 11.9 | |
| 2,4-Dimethylpentane | 12.2 | | 0.5 | | 12.1 | |
| 223-Trimethylbutane | 0.1 | | 0.0 | | 0.1 | |
| C7 Other | 0.7 | | 15.9 | | 0.7 | |
| Total C7 | | 24.9 | | 17.2 | | 24.9 |
| 223-Trimethylpentane | 1.4 | | 0.1 | | 1.4 | |
| 224-Trimethylpentane | 20.1 | | 0.7 | | 20.1 | |
| 233-Trimethylpentane | 5.2 | | 0.2 | | 5.2 | |
| 234-Trimethylpentane | 5.5 | | 0.2 | | 5.5 | |
| Dimethylhexanes | 8.0 | | 0.6 | | 8.1 | |
| C8 Other | 1.1 | | 26.3 | | 1.0 | |
| Total C8 | | 41.4 | | 28.2 | | 41.4 |
| 225-Trimethylhexane | 5.3 | | 0.4 | | 5.4 | |
| 235-Trimethylhexane | 0.8 | | 0.1 | | 0.8 | |
| 244-Trimethylhexane | 0.2 | | 0.1 | | 0.2 | |
| 223-Trimethylhexane | 0.0 | | 0.0 | | 0.0 | |
| 224-Trimethylhexane | 0.1 | | 3.3 | | 0.1 | |
| C9 Other | 1.5 | | 19.8 | | 1.6 | |
| Total C9 | | 7.9 | | 23.6 | | 8.0 |
| Total C10-C12 | 8.9 | 8.9 | 6.0 | 6.0 | 8.6 | 8.6 |
| Total C12+ | 1.4 | 1.4 | 2.8 | 2.8 | 1.4 | 1.4 |
| sum | 100.0 | 100.0 | 100.0 | 100.0 | 100.0 | 100.0 |
| % 224-TMP/total TMP | 62 | | 58 | | 62 | |
| % Trimethylpentane/total C8 | 78 | | 4 | | 78 | |
| % Trimethylhexane/total C9 | 81 | | 16 | | 81 | |

The composition of the alkylate gasoline showed that the ionic liquid catalyst has high selectivity for $C_7$ and $C_8$ isoparaffins via direct alkylation of $C_3$ and $C_4$ olefins with isobutane. The $C_8$ and $C_9$ hydrocarbon species are mainly trimethyl isomers in that the percentage of trimethylpentane in total $C_8$ is 78 wt % and the percentage of trimethylhexane in total $C_9$ is 81 wt %. Among the trimethylpentane isomers, 2,2,4-Trimethylpentane is the most common isomer. The percentage of 2,2,4-Trimethylpentane relative to the total $C_8$ trimethylpentane isomers is 62%. This value of 2,2,4-Trimethylpentane relative to the total $C_8$ trimethylpentane is much higher than that of alkylate produced by the sulfuric acid alkylation process. Sulfuric alkylation processes generally produce alkylate with 50 wt % or less of 2,2,4-Trimethylpentane relative to the total $C_8$.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

It is claimed:

1. An alkylation process unit, comprising:
    a) a hydrogenation reactor (100), wherein a used catalyst (70) comprising an ionic liquid catalyst and a chloride produces a regenerated catalyst effluent (10);
    b) a fractionation unit (200) fluidly connected to the hydrogenation reactor (100), that separates at least a portion of the regenerated catalyst effluent (10) into a gas fraction comprising a hydrogen gas (20) and into a light hydrocarbon fraction comprising a hydrogen chloride (30);
    c) a first connection between the fractionation unit (200) and the hydrogenation reactor (100) for transmitting at least a part of the gas fraction to the hydrogenation reactor (100); and
    d) a second connection between the fractionation unit (200) and an alkylation reactor (300) to transmit at least an amount of the light hydrocarbon fraction to the alkylation reactor (300).

2. The alkylation process unit of claim 1, additionally comprising one or more separators between the hydrogenation reactor (100) and the fractionation unit (200), fluidly connected to the hydrogenation reactor (100) and the alkylation reactor (300); wherein the one or more separators produce an offgas (50) that is fed to the fractionation unit (200) and also produce an ionic liquid catalyst stream (60) that is fed to the alkylation reactor (300).

3. The alkylation process unit of claim 1, additionally comprising a compressor located before the hydrogenation reactor (100), that compresses the at least the part of the gas fraction comprising the hydrogen gas (20) before recycling the at least the part of the gas fraction to the hydrogenation reactor (100).

4. The alkylation process unit of claim 1, additionally comprising a third connection between a product treatment unit and the second connection wherein the light hydrocarbon fraction is mixed with a recycled stream from the product treatment unit comprising a mixture of a light hydrogen chloride and a propane.

5. The alkylation process unit of claim 1, additionally comprising a selective olefin isomerization reactor (800), fluidly connected to the fractionation unit (200), that produces isomerized olefins (12) that are fed to the fractionation unit (200).

6. An alkylation process unit, comprising:
  a) a hydrogenation reactor (100), wherein a used catalyst (70) comprising an ionic liquid catalyst and a chloride produces a regenerated catalyst effluent (10);
  b) a separator (400), fluidly connected to the hydrogenation reactor (100) and a fractionation unit (200); wherein the separator (400) separates the regenerated catalyst effluent (10) into a gas fraction comprising a hydrogen gas (20) and into a separated liquid (85); and wherein the fractionation unit (200) separates a hydrocarbon stream (52) from the separated liquid (85) into a light hydrocarbon fraction comprising a hydrogen chloride and an extracted conjunct polymer naphtha (45);
  c) a first connection between the separator and the hydrogenation reactor (100) for transmitting at least a part of the gas fraction to the hydrogenation reactor (100); and
  d) a second connection between the fractionation unit (200) and an alkylation reactor (300) to transmit at least an amount of the light hydrocarbon fraction to the alkylation reactor (300).

7. The alkylation process unit of claim 6, additionally comprising a compressor located before the hydrogenation reactor (100), that compresses the at least the part of the gas fraction comprising the hydrogen gas (20) before recycling the at least the part of the gas fraction to the hydrogenation reactor (100).

8. The alkylation process unit of claim 6, additionally comprising a selective olefin isomerization reactor (800), fluidly connected to the fractionation unit (200), that produces isomerized olefins (12) that are fed to the fractionation unit (200).

* * * * *